US006774111B1

(12) United States Patent
Wolf et al.

(10) Patent No.: US 6,774,111 B1
(45) Date of Patent: Aug. 10, 2004

(54) CARBOHYDRATE SYSTEM AND A METHOD FOR PROVIDING NUTRITION TO A DIABETIC

(75) Inventors: Bryan W. Wolf, Johnstown, OH (US); Bradley A. Zinker, Vernon Hills, IL (US); Keith A. Garleb, Powell, OH (US); Joseph E. Walton, Westerville, OH (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/524,716

(22) Filed: Mar. 14, 2000

(51) Int. Cl.[7] .................. A61K 31/70; A61K 38/00; A23L 1/09; A23L 1/29

(52) U.S. Cl. .................. 514/23; 424/601; 424/630; 424/638; 424/639; 424/641; 424/643; 424/646; 424/655; 424/663; 424/682; 424/702; 424/722; 426/72; 426/73; 426/74; 426/601; 426/648; 426/656; 426/658; 514/2; 514/52; 514/54; 514/167; 514/168; 514/251; 514/255.05; 514/262.1; 514/276; 514/345; 514/356; 514/387; 514/458; 514/474; 514/556; 514/563; 514/567; 514/570; 514/574; 514/578; 514/642; 514/676; 514/685; 514/725; 514/727; 514/738; 514/866; 514/904; 514/905

(58) Field of Search .................. 424/601, 630, 424/638, 639, 641, 643, 646, 655, 663, 682, 702, 722, 439; 426/72, 73, 74, 601, 648, 656, 658; 514/2, 23, 52, 54, 167, 168, 251, 255.05, 262.1, 276, 345, 356, 387, 458, 474, 556, 563, 567, 570, 574, 578, 642, 676, 685, 725, 727, 738, 866, 904, 905, 60

(56) References Cited

U.S. PATENT DOCUMENTS

| | | | |
|---|---|---|---|
| 4,921,877 A | 5/1990 | Cashmere et al. | 424/439 |
| 5,270,297 A | 12/1993 | Paul et al. | 514/23 |
| 5,292,538 A | 3/1994 | Paul et al. | 426/74 |
| 5,292,723 A | 3/1994 | Audry et al. | 514/58 |
| 5,470,839 A | 11/1995 | Laughlin et al. | 514/53 |
| 5,695,803 A | 12/1997 | Sharp et al. | 426/549 |
| 5,776,887 A | 7/1998 | Wibert et al. | 514/2 |
| 5,843,921 A | * 12/1998 | Kaufman | 514/60 |
| 6,248,375 B1 | * 6/2001 | Gilles et al. | 426/72 |

FOREIGN PATENT DOCUMENTS

| WO | WO 98/17286 | 4/1998 |
|---|---|---|
| WO | WO 00/19841 | 4/2000 |

OTHER PUBLICATIONS

STN/CAS online, file LIFESCI, Acc. No. 81:44972, (Hicks et al.,'Corn sweeteners in ham formulas', J. Food Sci. (1981), vol. 46, No. 5, p. 1626), Abstract.*
Wolever, et al., "The use of the glycemic index in predicting the blood glucose response to mixed meals", The American Journal of Clinical Nutrition 43: Jan. 1986, pp. 167–172.
RESOURCE Diabetic, Clinical Products Division, Novartis Nutrition, 1998.
GLUCERNA® Product Information, Ross Products Division Abbott Laboratories, Apr. 1997.
Compelling Comparisons Glucerna® Specialized Nutrition With Fiber for Patients with Abnormal Glucose Tolerance, Ross Products Division Abbott Laboratories, Apr. 1998.
Ensure Glucerna® OS Beverages, Ross Products Division Abbott Laboratories, Aug. 1998.
Moore, et al., "Effect of Fructose on the Response of Normal Adults to an Oral Glucose Tolerance Test", Diabetes Abstract Book 59th Scientific Sessions Saturday, Jun. 19–Tuesday, Jun. 22, 1999, p. A291.
AACC Method 32–07, Approved Methods of The American Association of Cereal Chemists, Ninth Edition, Mar. 1995.
Titgemeyer,et al., "Fermentability of various fiber sources by human fecal bacteria in vitro[1–3]", Am J Clin Nutr 1991, 53: 1418–24.
Nutritional Profile Choice dm® Beverage and Choice dm Nutrition Bar, 1997, 1998, 1999 Mead Johnson & Company.
Compelling Comparisons Glucerna® Specialized Nutrition With Fiber for Patients with Abnormal Glucose Tolerance, Ross Products Division Abbott Laboratories Mar. 1996.

* cited by examiner

Primary Examiner—Thurman K. Page
Assistant Examiner—Frank Choi
(74) Attorney, Agent, or Firm—Thomas D. Brainard; Nickki L. Parlet

(57) ABSTRACT

The two carbohydrate mixture of this invention utilizes a source of fructose in combination with at least one readily digestible glucose polymer source. The addition of the fructose significantly decreases the glycemic response when compared to the digestible glucose polymer alone. Additional components may be added to the simple two component carbohydrate mixture to form a carbohydrate system suitable for incorporation into an enteral nutritional. This carbohydrate system optionally incorporates nonabsorbent carbohydrates, dietary fiber and indigestible oligosaccharides. The present invention is also directed to an enteral nutritional which incorporates the two component carbohydrate mixture and less than 37% of calories from fat. Additionally, the invention is directed to a method of delivering nutrients to a person with diabetes by feeding the enteral nutritional.

4 Claims, 4 Drawing Sheets

CARBOHYDRATE SYSTEM AND A METHOD FOR PROVIDING NUTRITION TO A DIABETIC

CROSS REFERENCE

This application is related to U.S. Pat. No. 6,248,375, issued Jun. 19, 2001, filed concurrently herewith by Gilles et. al., the contents of which are hereby incorporated by reference.

This invention relates to a two component carbohydrate mixture which blunts the postprandial glycemic response of digestible glucose polymers. The two component carbohydrate mixture is optionally admixed with nonabsorbent carbohydrates, fiber and indigestible oligosaccharides to form a carbohydrate system for diabetics. Additionally, the invention relates to nutritional formulas which incorporate the two component carbohydrate mixture or the carbohydrate system. Further, this invention relates to a method of delivering nutrition to an individual with diabetes by feeding said nutritional formulas.

BACKGROUND

Primary treatment for glucose intolerance is strict adherence to a diet which minimizes postprandial glucose response, and in many cases, use of medications (insulin or oral hypoglycemic agents).

Before 1921, starvation was the only recognized treatment of diabetes mellitus (DM). Since the discovery of exogenous insulin, diet has been a major focus of therapy. Recommendations for the distribution of calories from carbohydrate and fat have shifted over the last 75 years. Based on the opinions of the time, the best mix to promote metabolic control are listed in Table 1 below.

TABLE 1

History of Recommended Caloric Distribution of Persons with DM

| Year | Carbohydrate (%) | Protein (%) | Fat (%) |
|------|------------------|-------------|---------|
| 1921 | 20 | 10 | 70 |
| 1950 | 40 | 20 | 40 |
| 1971 | 45 | 20 | 35 |
| 1986 | 50–60 | 12–20 | 30 |
| 1994 | * | 10–20 | *^ |

*based on nutritional assessment
^<10% saturated fat

Early recommendations limited dietary carbohydrate, because glycemic control was generally better with this type of regimen. However, over the years researchers found that low-carbohydrate, high-fat diets were associated with dyslipidemias and cardiovascular disease, because most high-fat diets consumed in industrialized countries were high in saturated fat. In 1950, the American Diabetes Association (ADA) recommended increasing the proportion of calories provided by carbohydrate to lower cardiovascular risk. While the risk for cardiovascular disease might be diminished by this strategy, research demonstrated that not all persons with DM respond favorably from the standpoint of metabolic control. In addition, the saturated fat being consumed continued to contribute to cardiovascular risk. The ADA's recommendation to restrict total fat, without regard to type of fat was challenged in the late 1980s by investigators and participants in the National Institutes of Health (NIH) Consensus Development Conference on diet and exercise in patients with type 2 DM. The recommendation of a carbohydrate-rich diet for all persons with DM also was criticized because the theory that high-carbohydrate diets improve glycemic control and insulin sensitivity was not accepted due to inconclusive evidence. The NIH Conference led to the investigation of other dietary therapies, which resulted in a radical change in the 1994 ADA nutrition recommendations. The new ADA guidelines emphasize individualization of diet strategies. The purpose is to achieve optimal glycemic and metabolic control by varying the proportion of calories provided by the macro nutrients. The proportion selected depends on goals for glycemic control, dietary preferences and response to the diet.

The American Diabetes Association (ADA) currently recommends a diet in which protein is the same as that for the general population and accounts for 10% to 20% of total calories. With protein contributing 10% to 20% of the total calories, 80% to 90% of the total calories remains to be distributed between carbohydrate and fat. The carbohydrate/fat mix is individualized according to dietary preference, treatment goals, metabolic control and the presence of other medical conditions. However, the ADA does make a recommendation for the various types of fat in the diet. Specifically, saturated fat should contribute less than 10% of total calories, and polyunsaturated fat contributing no more than 10% of total calories. The remainder of fat calories should come from monounsaturated fat and the daily intake of cholesterol should be limited to less than 300 mg. The recommendation for fiber intake is the same as for the general public with approximately 20 to 35 g/day of dietary fiber from a variety of food sources. The micro nutrient requirements of otherwise healthy persons with DM will likely be met by consuming the amounts suggested by the Reference Daily Intakes (RDIs). The relationship of the minerals chromium and magnesium to management of DM has been the focus of much research. Individuals considered at risk for micro nutrient deficiencies should be evaluated to determine if supplementation is necessary.

Products designed as sole source of nutrition and as nutritional supplements for the person with diabetes are commercially available. The commercial products are typically liquid and include higher amounts of fat. The higher fat is desired in a liquid nutritional as the fat slows down stomach emptying. Thereby delaying the delivery of nutrients to the small intestine which blunts the absorption curve of carbohydrates after a meal.

Glucerna® (Ross Products Division of Abbott Laboratories, Columbus Ohio) is a liquid nutritional with fiber for patients with abnormal glucose tolerance. Sodium and calcium caseinates make up 16.7% of total calories as protein; maltodextrin, soy polysaccharide and fructose make up 34.3% of total calories as carbohydrate; and high oleic safflower oil and canola oil make up 49% of total calories as fat. Soy polysaccharide contributes 14.1 g/1000 ml of total dietary fiber. The RDI for vitamins and minerals is delivered in 1422 kcals. The product also contains the ultra trace minerals selenium, chromium and molybdenum and the conditionally essential nutrients carnitine and taurine.

Choice dm® (Mead Johnson & Company, Evensville, Ind.) is a nutritionally complete beverage for persons with glucose intolerance. Milk protein concentrate makes up 17% of total calories as protein; maltodextrin and sucrose make up 40% of total calories as carbohydrate; and high oleic sunflower oil and canola oil make up 43% of total calories as fat. Microcrystalline cellulose, soy fiber and gum acacia contribute 14.4 g/1000 ml of total dietary fiber. The RDI for vitamins and minerals is delivered in 1060 kcals. The product also contains the ultra trace minerals selenium, chromium and molybdenum and the conditionally essential nutrients, carnitine and taurine.

Resource® Diabetic (Sandoz Nutrition Corporation, Berne, Switzerland) is a complete liquid formula with fiber specifically designed for persons with type 1 and type 2 diabetes and for persons with stress-induced hyperglycemia. Sodium and calcium caseinates, and soy protein isolate make up, 24% of total calories as protein; hydrolyzed corn starch and fructose make up 36% of total calories as carbohydrate; and high oleic sunflower oil and soybean oil make up 40% of total calories as fat. Partially hydrolyzed guar gum contributes 3.0 g/8 ft. oz. of total dietary fiber. The RDI for vitamins and minerals is delivered in 2000 kcals. The product also contains the ultra trace minerals selenium, chromium and molybdenum and the conditionally essential nutrients carnitine and taurine.

Ensure® Glucerna® OS (Ross Products Division of Abbott Laboratories, Columbus Ohio) is an oral supplement specifically designed for people with diabetes. Sodium and calcium caseinates make up 18% of total calories as protein; maltodextrin, fructose, soy polysaccharide and gum arabic make up 37% of total calories as carbohydrate; and high oleic safflower oil and canola oil make up 45% of total calories as fat. Soy polysaccharide and gum arabic contribute 2.0 g/8 fl. oz. of total dietary fiber. At least 25% of the RDIs for 24 key vitamins and minerals are delivered in 8 fl. oz. The product also contains the ultra trace minerals selenium, chromium and molybdenum and the conditionally essential nutrients carnitine and taurine.

U.S. Pat. No. 4,921,877 to Cashmere et al. describes a nutritionally complete liquid formula with 20 to 37% of total caloric value from a carbohydrate blend which consists of corn starch, fructose and soy polysaccharide; 40 to 60% of total caloric value from a fat blend with less than 10% of total calories derived from saturated fatty acids,. up to 10% of total calories from polyunsaturated fatty acids and the balance of fat calories from monounsaturated fatty acids; 8 to 25% of total caloric value is protein; at least the minimum US RDA for vitamins and minerals; effective amounts of ultra trace minerals chromium, selenium and molybdenum; and effective amounts of carnitine, taurine and inositol for the dietary management of persons with glucose intolerance.

U.S. Pat. No. 5,776,887 to Wibert et al. describes a nutritional composition for the dietary management of diabetics containing a 1 to 50% total calories protein; 0 to 45% total calories fat, 5 to 90% total calories carbohydrate system and fiber. The carbohydrate system requires a rapidly absorbed fraction such as glucose or sucrose, a moderately absorbed fraction such as certain cooked starches or fructose and a slowly absorbed fraction such as raw corn starch.

U.S. Pat. No. 5,292,723 to Audry et al. describes a liquid nutritional composition containing a lipid fraction, a protein fraction and a specific combination of glucides useful as dietetics. The glucide fraction consists of glucose polymers and slowly absorbed glucides.

U.S. Pat. No. 5,470,839 to Laughlin et al. describes a composition and method for providing nutrition to a diabetic patient. The low carbohydrate, high fat enteral composition contains a protein source, a carbohydrate source including a slowly digested high amylose starch and soluble dietary fiber, and a fat source that includes a high percentage of monounsaturated fats.

The commercial products listed above begin to address the changing recommendations of the ADA for caloric distribution of persons with DM. The carbohydrate content has been increased slightly along with a corresponding slight decrease in fat, while the fat systems have been modified to decrease the contribution of saturated fatty acids. However, the caloric contribution of the fat remains above the ADA recommendations. The prior art also describes complex multi-component carbohydrate systems which blunt the glycemic response by requiring three or more sources of carbohydrate that are absorbed at different rates. These complex multi-component carbohydrate systems possess physical characteristics which make incorporation of the carbohydrate systems into nutritional formulas difficult. Additionally, these complex multi-component carbohydrate systems are often found to possess unacceptable organoleptic characteristics.

Thus, a need has developed in the art for a simple two component carbohydrate system which acts to blunt the glycemic response of readily absorbed carbohydrates. Particularly, a need has developed in the art for a nutritional product which provides nutrients to a person with abnormal glucose tolerance that also adheres to the ADA recommendations for fat.

SUMMARY OF THE INVENTION

The present invention is directed to a two component carbohydrate mixture that solves a number of problems associated with the prior art complex multi-component carbohydrate systems designed for the diabetic. The two component carbohydrate mixture of this invention utilizes a source of fructose in combination with at least one readily digestible glucose polymers. The use of the fructose in the two component carbohydrate mixture significantly decreases the glycemic response when compared to, the glucose polymer alone. Further, this two component carbohydrate mixture tastes good and possesses physical properties which allow for easy incorporation into liquid, powder, bars and semisolid nutritionals.

Additional components may be added to the two component carbohydrate mixture to form a "carbohydrate system". This carbohydrate system optionally incorporates nonabsorbent carbohydrates, dietary fiber and indigestible oligosaccharides, thereby increasing fecal bulk, modifying the transit time of nutrients through the intestines and providing nutrients to the beneficial microflora of the large intestine which all contribute to a healthy gastrointestinal tract.

The present invention is also directed to a new nutritional product designed for the person with diabetes that solves a number of problems associated with the prior art nutritional formulas. Since the aim of diabetic therapy is to prevent large fluctuations in blood glucose throughout the day, diabetics are advised to select carbohydrate foods that minimize blood glucose level after a meal by emphasizing the complex carbohydrates (starch) over the simple sugars. Complex carbohydrates are the preferred carbohydrate source as they are considered to be digested more slowly and to raise the blood glucose less than simple rapidly absorbed sugars. The prior art teaches that a complex multi-component carbohydrate system should be used. These systems incorporate differing carbohydrate sources that are digested and absorbed at differing rates. While theses systems produce improved blood glucose levels after a meal, they are difficult to incorporate into nutritional formulas.

The nutritional product of this invention utilizes a two component carbohydrate mixture which includes a source of fructose in combination with at least one readily digestible glucose polymers which the inventors have discovered significantly decreases the glycemic response when compared to the glucose polymer alone. Consequently, a nutritional formula may contain a higher percentage of readily absorbed carbohydrate and produce a lower glycemic response than expected. Further, the additional carbohydrate calories may replace fat calories, thereby facilitating the formulation of a nutritional for persons with diabetes containing less than 37% of the calories from fat.

The present invention is also directed, to a method of delivering nutrients to a person with abnormal glucose tolerance by feeding a nutritional which incorporates the two component carbohydrate mixture and less than 37% of calories from fat.

BRIEF DESCRIPTION OF THE DRAWINGS

To acquaint persons skilled in the art with the principles of the invention, a presently preferred embodiment illustrative of the invention follows with reference being made to the attached drawings forming a part of the specification and of which.

DETAILED DESCRIPTION

Figure 1:
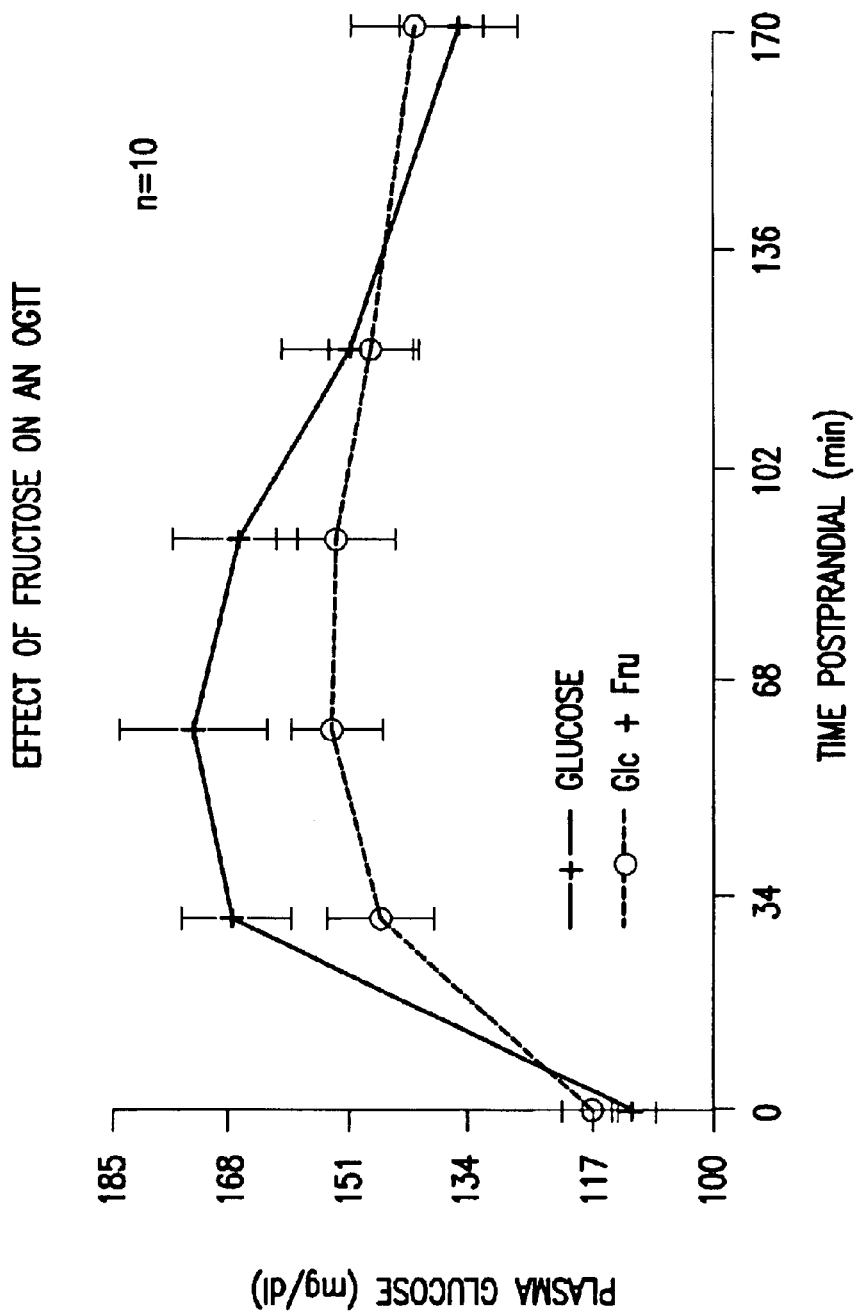
FIG. 1 is a graphical representation of the postprandial glycemic response of female Zucker fatty fa/fa rats fed glucose ± fructose set forth in Example V.

As used in this application:

a. the term "digestible glucose polymers" refers to hydrolyzed starches and glucose oligomers which are rapidly digested.

b. the term "dextrose equivalence" (DE) refers to a quantitative measure of the degree of starch polymer hydrolysis. It is a measure of reducing power compared to a dextrose (glucose) standard of 100. The higher the DE, the greater the extent of starch hydrolysis. As the starch is further hydrolyzed (higher DE), the average molecular weight decreases and the carbohydrate profile changes accordingly. Maltodextrin have a DE less than 20. Corn syrup solids have a DE of 20 or higher and are more rapidly absorbed.

c. "glycemic index" (GI) is calculated by dividing the blood glucose incremental area under the curve (AUC) of the test food by the blood glucose incremental AUC of the reference food and multiplying by 100, where the carbohydrate content of test and reference foods are the same. The reference food is typically glucose or white bread which has the standard GI of 100.

d. the term "total dietary fiber" or "dietary fiber" refers to the sum of the soluble and insoluble fibers. These food components are not broken down by the alimentary enzymes of the human to small molecules which are absorbed into the bloodstream.

e. "soluble" and "insoluble" dietary fiber is determined using American Association of Cereal Chemists (AACC) Method 32-07. A "soluble" dietary fiber source refers to a fiber source in which at least 60%, of the dietary fiber is soluble dietary fiber as determined by AACC Method 32-07, and an "insoluble" dietary fiber source refers to a fiber source in which at least 60% of the total dietary fiber is insoluble dietary fiber as determined by AACC Method 32-07.

f. "fermentable" and "non-fermentable" dietary fiber is determined by the procedure described in "Fermentability of Various Fiber Sources by Human Fecal Bacteria In Vitro", at AMERICAN JOURNAL CLINICAL NUTRITION, 1991; 53:1418–1424. This procedure is also described in U.S. Pat. No. 5,085,883 to Garleb, et al., the teachings of both of which are incorporated herein by reference. "Non-fermentable" dietary fiber refers to dietary fibers which have a relatively low fermentability of less than 40% by weight, preferably less than 30% by weight, and the term "fermentable" dietary fiber refers to dietary fibers which have a relatively high fermentability of greater than 60% by weight, preferably greater than 70% by weight.

g. the term "indigestible oligosaccharide" refers to a small carbohydrate moiety with a degree of polymerization less than or equal to about 20 and/or a molecular weight less than or equal to about 3,600, that is resistant to endogenous digestion in the human upper digestive tract.

h. the term "nonabsorbent carbohydrates" refers to a carbohydrate moiety with a degree of polymerization greater than about 20 and/or a molecular weight greater than about 3,600, that is resistant to endogenous digestion in the human upper digestive tract. Nonabsorbent carbohydrates possess many of the characteristics of total dietary fiber. However, they are not quantifiable by the AACC Method 32-07 for fiber and consequently they are not included in total dietary fiber values of the instant invention.

i. the term "total calories" refers to the total caloric content of a definitive volume of the finished nutritional product.

j. the term "Reference Daily Intakes or RDI" refers to a set of dietary references based on the Recommended Dietary Allowances for essential vitamins and minerals. The Recommended Dietary Allowances are a set of estimated nutrient allowances established by the National Academy of Sciences, which are updated periodically to reflect current scientific knowledge.

k. the terms "fructose" and "source of fructose" are used interchangeably and refer to the actual fructose content in a carbohydrate source.

One embodiment of the instant invention is a two component carbohydrate mixture which decreases the glycemic response of digestible glucose polymers. The two component carbohydrate mixture comprises a source of fructose and at least one digestible glucose polymer source. Component ranges for the two component carbohydrate system are described in Table 2 on a dry matter basis.

TABLE 2

| | Carbohydrate mixture ranges (wt/wt % of carbohydrate) | | |
|---|---|---|---|
| Component | Target (wt/wt %) | Preferred (wt/wt %) | More Preferred (wt/wt %) |
| fructose | 5–50 | 5–30 | 10–25 |
| digestible glucose polymer | 50–95 | 70–95 | 75–90 |

The preferred ranges may also be described as the ratio of digestible glucose polymer to fructose. The preferred range is from about 19:1 to 1:1 of digestible glucose polymer to fructose, more preferably from about 19:1 to 2.3:1, digestible glucose polymer to fructose, most preferably from about 9:1 to 3:1 digestible glucose polymer to fructose.

A component of the two component carbohydrate mixture of the invention is digestible glucose polymer. Any digestible glucose polymer suitable for human consumption may be utilized in the instant invention. Examples of typical digestible glucose polymer sources include corn syrup, corn syrup solids, rice syrup, glucose oligomers such as maltose and the sugar alcohols such as maltitol. As indicated in Table 2, the typical amount of digestible glucose polymer in the two component carbohydrate mixture is from about 50 wt/wt% to about 95 wt/wt% of the two component carbohydrate mixture, preferably from about 70 wt/wt% to about 95 wt/wt% of the two component carbohydrate mixture, more preferably from about 75 wt/wt% to about 90 wt/wt% of the two component carbohydrate mixture.

Glucose (dextrose) is found naturally in grains, fruits and honey. More typically, commercially available glucose is produced by complete hydrolysis of starch. During the hydrolysis process, digestible glucose polymers are generated as constituents of corn syrup. The amounts of glucose and glucose polymers in corn syrup can vary as described in Table 3 below.

TABLE 3

Carbohydrate profile of several sources*

| % dry basis | liquid dextrose | corn syrup DE 63 | corn syrup DE 43 | corn syrup DE 36 | corn syrup DE 45 | maltose |
|---|---|---|---|---|---|---|
| fructose | 0.1 | 0 | 0 | 0 | 0 | 0 |
| dextrose | 99 | 36 | 19 | 14 | 9 | 4 |
| maltose | 0.6 | 31 | 14 | 11 | 43 | 65 |
| maltotriose | 0.2 | 13 | 12 | 10 | 18 | 15 |
| higher saccharides | 0.1 | 20 | 55 | 65 | 30 | 16 |

*Data from Cargill, Minneapolis, Minnesota product information sheets

Any reference in this application to a quantity of digestible glucose polymer should be understood as referring to the actual amount of digestible glucose polymer in the carbohydrate source. One skilled in the art can readily calculate how much of a carbohydrate source should be added to the nutritional product in order to deliver the desired amount of digestible glucose polymer.

Maltose is a disaccharide which is comprised of two D-glucose units chemically linked together. Maltose is also produced by the hydrolysis of starch and a typical composition is listed in Table 3. Maltitol is the sugar alcohol of maltose produced by the hydrogenation of one of the glucose units of maltose.

Typically, the digestible glucose polymers of the instant invention are partially hydrolyzed starches. For example, the production of partially hydrolyzed corn starch typically begins with a corn starch slurry that is hydrolyzed with food grade acids and/or enzymes. The resulting syrup is refined by filtering and carbon treatment. The hydrolysis is controlled to achieve the desired endpoint. The partially hydrolyzed corn starch is classified according to its dextrose equivalence (DE) which represents the degree of hydrolysis. As described in Table 3, the corn 'syrup may be enriched in a particular constituent. These partially hydrolyzed starches are usually rapidly digested (some chemical modifications may decrease their digestibility resulting in nonabsorbent carbohydrates which are discussed later).

Commercial sources for the digestible glucose polymers are readily available and known to one practicing the art. For example, corn syrup solids are available from Cerestar USA, Inc in Hammond, Ind. Rice based syrups are available from California Natural Products in Lathrop, Calif. Maltose and corn syrup are available from Cargil in Minneapolis, Minn. Maltitol powder is available from Roquette America, Inc., Keokuk, Iowa. Maltitol syrup from AlGroup Lonza, Fair Lawn, N.J.

The second component of the two component carbohydrate mixture of the instant invention is source of fructose. Any fructose source suitable for human consumption may be utilized in the instant invention. Examples of typical fructose sources include sucrose, high fructose corn syrup and liquid and powder fructose. As indicated in Table 2, the typical amount of fructose in the two component carbohydrate mixture is from about 5 wt/wt% to about 50 wt/wt% of the two component carbohydrate mixture, preferably from about 5 wt/wt% to about 30 wt/wt% of the two component carbohydrate mixture, more preferably from about 10 wt/wt% to about 25 wt/wt% of the two component carbohydrate mixture.

Fructose is found in fruits and honey. More typically, commercially available fructose is produced by enzymatic conversion of saccharides to fructose. The fructose content of various sources is listed in Table 4 below.

TABLE 4

Carbohydrate profile of several fructose sources*

| % dry basis | fructose | high fructose corn syrup (representative profiles) | honey |
|---|---|---|---|
| fructose | 99.5 | 42 | 55 | 49 |
| dextrose | 0.5 | 52 | 41 | 40 |
| maltose | 0 | 3 | 2 | 9 |
| higher saccharides | 0 | 3 | 2 | 2 |

*Fructose and corn syrup data from Cargill, Minneapolis, Minnesota product information sheets, honey values from National Honey Board, San Francisco, California Commercial high fructose corn syrup is available with various levels of fructose. The high fructose corn syrup profiles listed in Table 4 represent two commercially available fructose sources, with fructose at 42% and 55% of the corn syrup, respectively. Any reference in this application to a quantity of fructose should be understood as referring to the actual fructose content within the carbohydrate source. For example, 100 gm of the honey in Table 4 would provide 49 gm of fructose. One skilled in the art can readily calculate how much of a carbohydrate source should be added to the nutritional product in order to deliver the desired amount of fructose.

Commercial sources for fructose are readily available and known to one practicing the art. For example, various high fructose corn syrups are available from Cargil in Minneapolis, Minn. Fructose is available from A.E. Staley in Decatur, Ill.

The present invention is also directed to a carbohydrate system which incorporates dietary fiber, nonabsorbent carbohydrates and indigestible oligosaccharides into the two component carbohydrate mixture described above. Typically for every gram of dietary fiber, nonabsorbent carbohydrate and indigestible oligosaccharide added to the formulation, a gram of the two component carbohydrate mixture is removed. Typically up to about 57 wt/wt% of the simple two component carbohydrate mixture may be replaced with a combination of dietary fiber, nonabsorbent carbohydrates and indigestible oligosaccharides to form a "carbohydrate systems".

The first optional component of the carbohydrate system is dietary fiber which comprises less than or equal to about 17 wt/wt% of the carbohydrate system, preferably less than or equal to about 15 wt/wt% of the carbohydrate system, more preferably less than or equal to about 10 wt/wt% of the carbohydrate system.

Examples of dietary fiber sources of the instant invention typically include gum arabic, carboxymethylcellulose, guar gum, konjac flour, xanthan gum, alginate, gellan gum, gum acacia, citrus pectin, low and high methoxy pectin, modified cellulose, oat and barley glucans, carrageenan, psyllium, soy polysaccharide, oat hull fiber, pea hull fiber, soy hull fiber, soy cotyledon fiber, sugar beet fiber, cellulose, corn bran and hydrolyzed forms of the listed fibers and any combination thereof.

Numerous types of dietary fibers are known and available to one practicing the art. Fibers differ significantly in their chemical composition and physical structure and therefore their physiological functions. The dietary fiber sources utilized in this invention can be characterized by the terms solubility and fermentability. With regard to solubility, fiber can be divided into soluble and insoluble types and fiber sources differ in the amount of soluble and insoluble fiber they contain.

Representative of soluble dietary fiber, sources are gum arabic, sodium carboxymethylcellulose, guar gum, gellan gum, konjac flour, xanthan gum, alginate, citrus pectin, low and high methoxy pectin, oat and barley glucans, carrageenan and psyllium. Numerous commercial sources of soluble dietary fibers are readily available and known to one practicing the art. For example, gum arabic, hydrolyzed carboxymethylcellulose, guar gum, xanthan gum, alginates, pectin and the low and high methoxy pectins are available from TIC Gums, Inc. of Belcamp, Md. The oat and barley glucans are available from Mountain Lake Specialty Ingredients, Inc. of Omaha, Nebr. Psyllium is available from the Meer Corporation of North Bergen, N.J. while the carrageenan and konjac flour are available from FMC Corporation of Philadelphia, Penn.

Representative of the insoluble dietary fibers are oat hull fiber, pea hull fiber, soy hull fiber, soy cotyledon fiber, sugar beet fiber, cellulose and corn bran. Numerous sources for the insoluble dietary fibers are readily available and known to one practicing the art. For example, the corn bran is available from Quaker Oats of Chicago, Ill.; oat hull fiber from Canadian Harvest of Cambridge, Minn.; pea hull fiber from Woodstone Foods of Winnipeg, Canada; soy hull fiber and oat hull fiber from The Fibrad Group of LaVale, Md.; soy cotyledon fiber from Protein Technologies International of St. Louis, Mo.; sugar beet fiber from Delta Fiber Foods of Minneapolis, Minn. and cellulose from the James River Corp. of Saddle Brook, N.J.

Dietary fiber can also be divided into fermentable and non-fermentable types. This property of fiber is the capacity to be fermented by the anaerobic bacteria present in the human large bowel. Dietary fibers vary significantly in their fermentability.

Representative of fermentable dietary fiber sources are gum arabic and guar gum. Commercial sources of fermentable dietary fibers are readily available and known to one practicing the art. For example, gum arabic and guar gum are available from TIC Gums, Inc. of Belcamp, Md.

Representative of non-fermentable dietary fiber sources are carboxymethylcellulose (CMC), psyllium, oat hull fiber and corn bran. Numerous commercial sources of non-fermentable dietary fibers are readily available and known to one practicing the art. For example, carboxymethylcellulose is available from TIC Gums, Inc. of Belcamp, Md. The corn bran is available from Quaker Oats of Chicago, Ill. while the oat hull fiber is available from Canadian Harvest of Cambridge, Minn. Psyllium is available from the Meer Corporation of North Bergen, N.J.

The second optional component of the carbohydrate system is nonabsorbent carbohydrates which comprises less than or equal to about 20 wt/wt% of the carbohydrate system, preferably less than or equal to 15 wt/wt% of the carbohydrate system, more preferably less than or equal to about 10 wt/wt% of the carbohydrate system.

Examples of nonabsorbent carbohydrates sources of the instant invention typically include chemically modified starches such as Fibersol 2(E) and inulin.

Nonabsorbent carbohydrates possess many of the characteristics of fibers but are not quantified by the AACC method as total dietary fiber. Chemical modification of starch can ultimately affect its rate and extent of digestion in the small intestine. Partial hydrolysis of starch using acid and heat results in molecular rearrangement of the starch molecule such that alpha and beta-(1,2) and -(1,3) linkages are formed in addition to reconfiguration of existing alpha-(1,4) and -(1,6) bonds in to beta bonds. For example, corn starch treated with hydrochloric acid, amylase and heat produces a low molecular weight indigestible dextrin (distributed by Matsutani Chemical Industry, Hyogo Japan under the product name Fibersol 2(E)) with a'slow rate of fermentation. Therefore, the sat nonabsorbent carbohydrate is more likely to reach the lower part of the large intestine and be utilized by the indigenous microbiota.

Inulin is usually purified from plants such as chicory, Jerusalem artichoke, leek and asparagus. Various procedures for extracting the inulin have been reported. Usually the steps include chopping up the plant, extracting it.

Commercial sources of nonabsorbent carbohydrates are readily available and known to one practicing the art. For example, Fibersol 2(E) is available from Matsutani Chemical Industry, Hyogo Japan while inulin is available from Rhone-Poulenc, Inc, Cranbury, N.J.

The third optional component of the carbohydrate system is indigestible oligosaccharides which comprises less than or equal to about 20 wt/wt% of the carbohydrate system, preferably less than or equal to 15 wt/wt% of the carbohydrate system, more preferably less than or equal to about 10 wt/wt% of the carbohydrate system.

Examples of indigestible oligosaccharide sources of the instant invention typically include fructooligosaccharides (FOS), xylooligosaccharides(XOS), alpha glucooligosaccharides(GOS), trans galactosyl oligosaccharides(TOS), soybean oligosaccharides, lactosucrose, hydrolyzed inulin and polydextrose.

An indigestible oligosaccharide, such as fructooligosaccharide(FOS), is rapidly and extensively fermented to short chain fatty acids by anaerobic microorganisms that inhabit the large bowel increasing cell proliferation in the proximal colonic epithelial mucosa. Further, FOS is a preferential energy source for most Bifidobcterium species but it is not utilized by potentially pathogenic organisms such as *Clostrdium perfingens, C. difficile*, or *E. coli*. Thus, the addition of FOS to the nutritional products of the present invention selects for beneficial bacteria, such as bifidobacteria, but against potential pathogens, such as *Clostridium difficile* and putrefactive bacteria.

Numerous commercial sources of indigestible oligosaccharides are readily available and known to one practicing the art. For example, FOS is available from Golden Technologies Company of Golden, Colorado and XOS is available from Suntory Limited of Osaka Japan. GOS is available from Solabia, Pantin Cedex, France. TOS is available from Yakult Honsha Co., Tokyo, Japan. Soybean oligosaccharide is available from Calpis Corporation distributed by Ajinomoto U.S.A. Inc., Teaneck, N.J. Hydrolyzed inulin is available from Rhone-Poulenc, Inc, Cranbury, N.J. while polydextrose is available from A.E. Staley in Decatur Ill.

The present invention is also directed to a method of blunting the glycemic response of digestible glucose polymers by feeding the two component carbohydrate mixture or carbohydrate system described above. Research in the area of glucose tolerance tests by Mary Moore et. al. ("Effect of Fructose on the Response of Normal Adults to an Oral Glucose Tolerance Test", A JOURNAL OF THE AMERICAN DIABETES ASSOCIATION, ABSTRACT BOOK 59TH SCIENTIFIC SESSIONS, Jun. 1999, Abstract 1270, p. A291) teaches that glucose tolerance was improved by the addition of fructose to a glucose solution in 8 normal subjects, unchanged in 1 normal subject and worsened in 2 normal subjects. Moore et. al. concluded that, fructose appears most effective in those normal individuals who have the largest glycemic excursions in response to glucose alone. Since glucose metabolism of a diabetic is significantly altered from that of a normal individual, the inventors tested the addition of fructose to a glucose challenge in a diabetic animal model (study described in Example V) and found a significant reduction in the incremental area under the curve (AUC) for blood glucose of 34% when compared to the control challenge. The inventors were also surprised to discover that supplemental fructose added to a partially hydrolyzed starch challenge significantly reduced the incremental area under the curve (AUC) for blood glucose by 32% when compared to the control challenge (study described in Example VI). One knowledgeable in the art would not have expected to see reductions in blood glucose levels similar to simple sugars for partially hydrolyzed starch.

As noted above, the present invention is also directed to a nutritional product utilizing the two component carbohydrate mixture or carbohydrate system defined above.

The carbohydrate calories replace the fat calories in the nutritional, thereby facilitating the formulation of a nutritional for persons with diabetes containing less than 37% of the calories from fat, which is a significant advantage over prior art nutritional formulas.

The nutritional products of this invention are designed to be used as a sole source of nutrition or as a supplement in persons with DM. Since the product can be used as a sole source of nutrition it will contain a protein source, a lipid source, a carbohydrate source, vitamins, and minerals in amounts sufficient to maintain a patient's health (i.e., to prevent malnutrition). Such amounts are well known by those skilled in the art and can be readily calculated when preparing such products.

Although not intended to limit the invention in any manner, but to merely serve as a general guideline, the nutritional formulas of this invention will typically provide the caloric distribution described in Table 5.

TABLE 5

Nutritional Formula Component Ranges

| Component | Preferred range (% Calories) | More preferred range (% Calories) |
| --- | --- | --- |
| Protein | 10–35 | 15–25 |
| Fat | ≦37 | 25–30 |
| Carbohydrate* | 25–60 | 35–55 |

*may be the two component carbohydrate mixture or carbohydrate system of the instant invention Additionally, the caloric density is typically from about 0.5 kcal/ml to about 2.0 kcal/ml, preferably from about 0.8 kcal/ml to about 1.2 kcal/ml.

One required component of the nutritional products of this invention is a source of carbohydrates. Either the simple two component carbohydrate mixture or carbohydrate system described above may be incorporated into the nutritional. As stated in Table 5, the carbohydrate component of the nutritional typically provides from about 25% to about 60% of the total calories, more preferably from about 35% to about 55% of the total calories of the nutritional product.

The preferred carbohydrate system for the nutritional typically comprises about 64 wt/wt% of the carbohydrate system as digestible glucose polymers; about 23 wt/wt% of the carbohydrate system as fructose; about 6.5 wt/wt% of the carbohydrate system as nonabsorbent carbohydrates; about 3.5 wt/wt% of the carbohydrate system as indigestible oligosaccharides; and about 3.0 wt/wt% of the carbohydrate system as fiber.

The second component of the nutritional products of this invention is protein. The proteins that may be utilized in the nutritional products of the invention include any proteins suitable for human consumption. Such proteins are well known by those skilled in the art and can be readily selected when preparing such products. Examples of suitable proteins that may be utilized typically include casein, whey, milk protein, soy, pea, rice, corn, hydrolyzed protein and mixtures thereof. As indicated in Table 5, the typical amount of protein in the nutritional product is from about 10% to about 35% of total calories, more preferably from about 15% to about 25% of total calories.

Commercial protein sources are readily available and known to one practicing the art. For example, caseinates, whey, hydrolyzed caseinates; hydrolyzed whey and milk proteins are available from New Zealand Milk Products of Santa Rosa, Calif. Soy and hydrolyzed soy proteins are available from Protein Technologies International of Saint Louis, Mo. Pea protein is available from Feinkost Ingredients Company of Lodi, Ohio. Rice protein is available from California Natural Products of Lathrop, Calif. Corn protein is available from EnerGenetics Inc. of Keokuk, Iowa.

The third component of the nutritional products of this invention is the fat. As noted above, the fat source of this invention will typically provide less than or equal to 37% of the total calories, more preferably from about 25% to about 30% of the total calories. The fat source for the present invention may be any fat source or blend of fat sources which provides the desired levels of saturated (less than 10% kcal), polyunsaturated (up to 10% kcal) and monounsaturated fatty acids (10% to 15% kcal). One skilled in the art can readily calculate how much of a fat source should be added to the nutritional product in order to deliver the desired levels of saturated, polyunsaturated and monounsaturated fatty acids. Examples of food grade fats are well known in the art and typically include soy oil, olive oil, marine oil, sunflower oil, high oleic sunflower oil, safflower oil, high oleic safflower oil, fractionated coconut oil, cottonseed oil, corn oil, canola oil, palm oil, palm kernel oil and mixtures thereof.

Numerous commercial sources for the fats listed above are readily available and known to one practicing the art. For example, soy and canola oils are available from Archer Daniels Midland of Decatur, Ill. Corn, coconut, palm and palm kernel oils are available from Premier Edible Oils Corporation of Portland, Oreg. Fractionated coconut oil is available from Henkel Corporation of LaGrange, Ill. High oleic safflower and high oleic sunflower oils are available from SVO Specialty Products of Eastlake, Ohio. Marine oil is available from Mochida International of Tokyo, Japan. Olive oil is available from Anglia Oils of North Humberside, United Kingdom. Sunflower and cottonseed oils are available from Cargil of Minneapolis, Minn. Safflower oil is available from California Oils Corporation of Richmond, Calif.

The nutritional compositions of the invention desirably contain vitamins and minerals. Vitamins and minerals are understood to be essential in the daily diet. Those skilled in the art appreciate that minimum requirements have been established for certain vitamins and minerals that are known to be necessary for normal physiological function. Practitioners also understand that appropriate additional amounts of vitamin and mineral ingredients need to be provided to nutritional compositions to compensate for some loss during processing and storage of such compositions. Additionally, the practitioner understands that certain micronutrients may have potential benefit for people with diabetes such as chromium, carnitine, taurine and vitamin E and that higher dietary requirements may exist for certain micro nutrients such as ascorbic acid due to higher turnover in people with type 2 diabetes.

An example of the vitamin and mineral system for a complete nutritional formulation used as a sole source of nutrition typically comprises at least 100% of the RDI for the vitamins A, $B_1$, $B_2$, $B_6$, $B_{12}$, C, D, E, K, beta-carotene, Biotin, Folic Acid, Pantothenic Acid, Niacin, and Choline; the minerals calcium, magnesium, potassium, sodium, phosphorous, and chloride; the trace minerals iron, zinc, manganese, copper, and iodine; the ultra trace minerals chromium, molybdenum, selenium; and the conditionally essential nutrients m-inositol, carnitine and taurine in from about 350 Kcal to about 5600 Kcal.

An example of the vitamin and mineral system for a nutritional formulation used as a nutritional supplement typically comprises at least 25% of the RDI for the vitamins A, $B_1$, $B_2$, $B_6$, $B_{12}$, C, D, E, K, beta-carotene, Biotin, Folic Acid, Pantothenic Acid, Niacin, and Choline; the minerals calcium, magnesium, potassium, sodium, phosphorous, and chloride; the trace minerals iron, zinc, manganese, copper, and iodine; the ultra trace minerals chromium, molybdenum, selenium; and the conditionally essential nutrients m-inositol, carnitine and taurine in a single serving or from about 50 Kcal to about 800 Kcal.

Artificial sweeteners may also be added to the nutritional formula to enhance the organoleptic quality of the formula. Examples of suitable artificial sweeteners include saccharine, aspartame, acesulfame K and sucralose. The nutritional products of the present invention will also desirably include a flavoring and/or color to provide the nutritional products with an appealing appearance and an acceptable taste for oral consumption. Examples of useful flavorings typically include, for example, strawberry, peach, butter pecan, chocolate, banana, raspberry, orange, blueberry and vanilla.

The nutritional products of this invention can be manufactured using techniques well known to those skilled in the art. While manufacturing variations are certainly well known to those skilled in the nutritional formulation arts, a few of the manufacturing techniques are described in detail in the Examples. Generally speaking an oil and fiber blend is prepared containing all oils, any emulsifier, fiber and the fat soluble vitamins: Three more slurries (carbohydrate and two protein) are prepared separately by mixing the carbohydrate and minerals together and the protein in water. The slurries are then mixed together with the oil blend. The resulting mixture is homogenized, heat processed, standardized with water soluble vitamins, flavored and the liquid terminally sterilized or dried to produce a powder. Alternatively, the homogenized formula may be kept undiluted and filled into appropriate containers as pudding or dried to form powder.

The composition of the invention can be in several physical forms such as liquid enteral nutritional formulas or concentrated-liquid, a semisolid form such as pudding or a solid form such as a powder or nutritional bar.

The present invention is also directed to a method of delivering nutrients to a person with diabetes by feeding the nutritional described above.

EXAMPLE I

Table 6 presents a bill of materials for manufacturing 1,000 kilograms of an unflavored liquid nutritional product according to the present invention. A detailed description of its manufacture follows.

TABLE 6

Bill␣f␣Mat rials␣f r Unflavor d Liquid Nutritional

| Ingredient | Quantity per 1,000 Kg |
|---|---|
| Water | 840 Kg |
| Maltrin-100 | 56 Kg |
| Acid Casein | 41.093 Kg |
| Fructose | 28 Kg |
| High Oleic Safflower Oil | 27.2 Kg |
| Maltitol Syrup | 16 Kg |
| Maltitol Powder | 12.632 Kg |
| Fibersol 2(E) | 8.421 Kg |
| Calcium caseinate | 6.043 Kg |
| Fructooligosaccharide | 4.607 Kg |
| Soy Polysaccharide | 4.3 Kg |
| Canola Oil | 3.2 Kg |
| micronized tricalcium phosphate | 2.8 Kg |
| magnesium chloride | 2.4 Kg |
| soy lecithin | 1.6 Kg |
| sodium citrate | 1.18 Kg |
| potassium citrate | 1.146 Kg |
| sodium hydroxide | 1.134 Kg |
| magnesium phosphate | 1.028 Kg |
| m-inositol | 914.5 gm |
| vitamin C | 584 gm |
| potassium chloride | 530 gm |
| choline chloride | 472.1 gm |
| 45% potassium hydroxide | 402.5 gm |
| utm/tm premix | 369.3 gm |
| potassium phosphate | 333 gm |
| carnitine | 230.5 gm |
| gellan gum | 125 gm |
| taurine | 100.1 gm |
| vitamin E | 99 gm |
| WSV premix | 75.4 gm |
| Vitamin DEK premix | 65.34 gm |
| 30% beta carotene | 8.9 gm |
| vitamin A | 8.04 gm |
| pyridoxine hydrochloride | 3.7 gm |
| chromium chloride | 1.22 gm |
| folic acid | 0.64 gm |
| potassium iodide | 0.20 gm |
| cyanocobalamin | 0.013 gm |

WSV premix(per g premix): 375 mg/g niacinamide, 242 mg/g calcium pantothenate, 8.4 gm/g folic acid, 62 mg/g thiamine chloride hydrochloride, 48.4 gm/g riboflavin, 59.6 mg/g pyridoxine hydrochloride, 165 mcg/g cyanocobalamin and 7305 mcg/g biotin Vitamin DEK premix (per g premix): 8130 IU/g vitamin $D_3$, 838 IU/g vitamin E, 1.42 mg/g vitamin $K_1$
UTM/TM premix(per g premix): 45.6 mg/g zinc, 54 mg/g iron, 15.7 manganese, 6.39 mg/g copper, 222 mcg/g selenium, 301 mcg/g chromium and 480 mcg/g molybdenium The liquid nutritional products of the present invention have been manufactured by preparing four slurries which are blended together, heat treated, standardized, packaged and sterilized. The process for manufacturing 1000 kilograms of a liquid nutritional product, using the bill of materials from Table, 6 is described in detail below.

A carbohydrate/mineral slurry is prepared by first heating about 82 kilograms of water to a temperature of from about 65° C. to about 71° C. with agitation. With agitation, the required amount of sodium citrate and gellen gum distributed by the Kelco, Division of Merck and Company Incorporated, San Diego, Calif., U.S.A. under the product name "Kelcogel." is added and agitated for 5 minutes. The required amount of the ultra trace mineral/trace mineral (UTM/TM) premix (distributed by Fortitech, Schnectady, N.Y.) is added. The slurry is greenish yellow in color. Agitation is maintained until the minerals are completely dispersed. With agitation, the required amounts of the following minerals are then added: potassium citrate, potassium chloride, chromium chloride; magnesium chloride and potassium iodide. Next, the first maltodextrin distributed by Grain Processing Corporation, Muscataine, Iowa, U.S.A. under the product name "Maltrin M-100" and fructose are added to slurry under high agitation, and are allowed to dissolve. With agitation, the required amounts of maltitol powder distributed by Roquette America, Inc., Keokuk, Iowa under the product name Maltisorb Powder P35SK, maltitol syrup distributed by AlGroup Lonza, Fair Lawn, N.J. under the product name Hystar 5875, fructooligosaccharides distributed by Golden Technologies Company, Golden, Colo., U.S.A. under the product designation "Nutriflora-P Fructo-oligosaccharide Powder (96%)" and a second maltodextrin distributed by Mactsutani Chemical Industry Co., Hyogo, Japan under the product name Fibersol 2(E) are added and agitated well until completely dissolved. The required amount of micronized tricalcium phosphate is added to the slurry under agitation. The completed carbohydrate/mineral slurry is held with agitation at a temperature from about 65° C. to about 71° C. for not longer than twelve hours until it is blended with the other slurries.

A fiber in oil slurry is prepared by combining and heating the required amounts of high oleic safflower oil and canola oil to a temperature from about 55° C. to about 65° C. with agitation. With agitation, the required amounts of the following ingredients are added to the heated oil: soy lecithin (distributed by Central Soya Company, Fort Wayne, Ind. under the product name Centrocap 162), Vitamin D, E, K premix (distributed by Vitamins Inc., Chicago, Ill.), vitamin A and beta-carotene. The required amounts of soy polysaccharide distributed by Protein Technrology International, St. Louis, Mo. under the product name Fibrim 300 is slowly dispersed into the heated oil. The completed oil/fiber slurry is held under moderate agitation at a temperature from about 55° C. to about 65° C. for a period of no longer than twelve hours until it is blended with the other slurries.

A first protein in water slurry is prepared by heating 293 kilograms of water to 60° C. to 65° C. With agitation, the required amount of 20% potassium citrate solution is added and held for one minute. The required amount of acid casein is added under high agitation followed immediately by the required amount of 20% sodium hydroxide. The agitation is maintained at high until the casein is dissolved. The slurry is held from about 60° C. to 65° C. with moderate agitation.

A second protein in water slurry is prepared by first heating about 77 kilograms of water to a temperature of about 40° C. with agitation. The calcium caseinate is added and the slurry is agitated well until the caseinate is completely dispersed. With continued agitation, the slurry is slowly warmed to 60° C. to 65° C. The slurry is held for no longer than twelve hours until it is blended with the other slurries.

The batch is assembled by blending 344 kilograms of protein slurry one with 84 kilograms of protein slurry two. With agitation, the 37 kilograms of the oil/fiber slurry is added. After waiting for at least one minute, 216 kilograms of the carbohydrate/mineral slurry is added to the blended slurry from the preceding step with agitation and the resultant blended slurry is maintained at a temperature from about 55° C. to about 60° C. The pH of the blended batch is adjusted to al pH of 6.45 to 6.75 with 1N potassium hydroxide.

After waiting for a period of not less than one minute nor greater than two hours, the blend slurry is subjected to deaeration, ultra-high-temperature treatment, and homogenization, as follows:

A. positive pump is used to supply the blended slurry for this procedure;

B. the blended slurry is heated to a temperature from about 71° C. to about 82° C.;

C. the heated slurry is deareated at 10–15 inches Hg

D. the heated slurry is emulsified at 900 to 1100 psig in a single stage homogenizer;

E. the emulsified slurry is passed through a plate/coil heater and preheated to from about 99° C. to about 110° C.;

F. the preheated slurry is ultra high temperature heated by steam injection to a temperature of about 146° C. with a minimum hold time of about 5 seconds;

G. the temperature of the UHT treated slurry is reduced to from about 99° C. to about 110° C. by passing it through a flash cooler;

H. the temperature of the UHT treated slurry is reduced further to from about 71° C. to about 76° C. by passing it through a plate/coil heat exchanger, I. the UHT treated slurry is homogenized at 3900 to 4100/400 to 600 psig;

J. the homogenized slurry is passed through a hold tube for at least 16 seconds at temperature from about 74° C. to about 80° C.;

K. the homogenized slurry is cooled to a temperature from about 1° C. to about 7° C. by passing it through a heat exchanger; and L. the UHT treated and homogenized slurry is stored at a temperature from about 1° C. to about 7° C. with agitation.

After the above steps have been completed, appropriate analytical testing for quality control is conducted.

A water soluble vitamin (WSV) solution is prepared separately and added to the processed blended slurry.

The vitamin solution is prepared by adding the following ingredients to 9.4 kilograms of water with agitation: WSV premix (distributed by J.B. Laboratories, Holland, Mich.), vitamin C, choline chloride, L-carnitine, taurine, inositiol, folic acid, pyridoxine hydrochloride and cyanocobalamin. The required amount of 45% potassium hydroxide slurry is added to bring the pH to between 7 and 10.

Based on the analytical results of the quality control tests, an appropriate amount of water is added to the batch with agitation to achieve about 21% total solids. Additionally, 8.8 kilograms of vitamin solution is added to the diluted batch under agitation.

The product pH may be adjusted to achieve optimal product stability. The completed product is then placed in suitable containers and subjected to terminal sterilization.

EXAMPLE II

An alternative product form of the nutritional described in Example I is a semisolid or pudding. The product is manufactured as in Example I up through the heat treatment and homogenization step with the following addition. Two additional starches (distributed by A. E. Staley, Decatur, Ill. under the product names of Resista and Miraclear) are added to the carbohydrate slurry at 4.5 wt/wt% of total solids of the product. The water soluble vitamins and optional flavor are added to the undiluted blend. The pudding is filled at about 30 wt/wt% to 32 wt/wt% total solids into an appropriate container and terminally sterilized. Alternatively, the pudding is aseptically filled into appropriate containers.

EXAMPLE III

Another product form of the nutritional described in Example I is a powder. The product is manufactured as in Example I up through the heat treatment and homogenization step. The water soluble vitamins and optional flavor are added to the undiluted blend. The blend is pumped to a tower dryer at about 45% to 55% total solids. The dryer parameters are as follows:

Nozzle pressure 1400–2400 psig

Liquid flow rate 10 gpm max.

Ingoing air temperature 211° C. max.

Outgoing air temperature 87–+104° C.

Dryer chamber pressure −0.2–+0.2 inches of water

To control bulk density, dispersibility, particle size, moisture and physical stability, the specific spray nozzle, nozzle pressure, drying temperatures and fine reinjection parameters may vary depending upon the drying conditions of the day. The powder passes from the dryer discharge cone into the powder cooler where it is cooled to about 43° C. The cooled powder is stored until it is filed into appropriate containers.

EXAMPLE IV

The nutritional of the instant invention may also be formulated as a nutritional bar. Although not intended to limit the invention in any manner, but to merely serve as a general guideline, a typical formulation for a nutritional bar is described in Table 7.

TABLE 7

Nutritional Bar Formulation

| Ingredient | Percent Formulation |
| --- | --- |
| maltitol | 24 |
| rolled oats | 21.5 |
| rice crisps | 20.5 |
| high oleic safflower oil | 7 |
| soy protein isolate | 5.5 |
| vitamin/mineral premix | 4.15 |
| fructose | 3.2 |
| glycerin | 2 |
| whey protein isolate | 2 |
| almonds | 2 |
| modified starch | 2 |
| calcium caseinate | 1.5 |
| plolydextrose | 1.4 |
| soy polysaccharide | 1 |
| canola oil | 0.9 |
| water | 0.8 |
| soy lecithin | 0.27 |
| vanilla flavoring | 0.2 |

The typically caloric distribution of a nutritional bar utilizing the ingredient percent of Table 7 is about 15% of the total calories as protein, about 25% of the total calories as fat and about 60% of the total calories as carbohydrate.

The nutritional bar composition is manufactured using cold extrusion technology as is known in the art. To prepare such compositions, typically all of the powdered components will be dry blended together. Such constituents typically include the proteins, vitamin premixes, certain carbohydrates, etc. The fat soluble components are then blended together and mixed with the powdered premix above. Finally any liquid components are then mixed into the composition, forming a plastic like composition or dough.

The process above is intended to give a plastic mass which can then be shaped, without further physical or chemical changes occurring, by the procedure known as cold forming or extrusion. In this process, the plastic mass is forced at relatively low pressure through a die which confers the desired shape and the resultant exudate is then cut off at an appropriate position to give products of the desired weight.

The mass may, for example, be forced through a die of small cross-section to form a ribbon, which is carried on a belt moving at a predetermined speed under a guillotine type cutter which operates at regular intervals. The cutter, in this case, generally consists of a sharpened blade so adjusted that it cuts through the ribbon but not the underlying belt, but may also consist of a wire. In both cases, the principle is the same; the cutting process occurs at intervals that permit the moving ribbon to be cut into pieces of equivalent weight and dimensions. Generally, this is achieved by timing the cutting strokes and maintaining belt speed at an appropriate level, but there also exist computer controlled versions of this mechanism which offer greater versatility. Alternatively, the mass may be forced through a die of large cross-section and then cut at die level into slices by an oscillating knife or wire, which drop onto a moving belt and are thus transported away. The mass may also be extruded as a sheet, which is then cut with a stamp type cutter into shapes that are appropriate, such as a cookie type cutter. Finally, the mass may also be forced into chambers on a rotary die equipped with an eccentric cam that forces the thus-formed material out of the chamber at a certain point in a rotation of the cylindrical die.

After shaping, the formed product is moved by a transfer belt or other type of material conveyor to an area where it may be further processed or simply packaged. In general, a nutritional bar of the type described would be enrobed (coated) in a material that may be chocolate, a compound chocolate coating, or some other type of coating material. In all such cases, the coating material consists of a fat that is solid at room temperature, but that is liquid at temperature in excess of e.g. 31° C., together with other materials that confer the organoleptic attributes. The coating is thus applied to the bar while molten, by permitting the bar to pass through a falling curtain of liquid coating, at the same time passing over a plate or rollers which permit coating to be applied to the under surface of the bar, and excess coating is blown off by means of air jets. Finally, the enrobed bar passes through a cooling tunnel where refrigerated air currents remove heat and cause the coating to solidify.

EXAMPLE V

The objective of this experiment was to evaluate the postprandial glycemic response of female Zucker fatty fa/fa rats fed glucose with supplemental fructose.

Ten female Zucker fatty fa/fa rats were obtained at nine weeks of age from Harlan Sprague Dawley, Inc. (Indianapolis, Ind.). Rats were individually housed in microisolator cages on dry bedding and were given ad libitum access to water and rat chow (pelletted; 8640 Harlan Teklad 22/5 Rodent Diet; Harlah Teklad, Madison, Wis.). The housing facility was maintained at 19° to 21° C., 30 to 70 % relative humidity, and 12 hour light-dark cycle. Rats were handled 4 to 5 times per week for 8 weeks prior to this experiment in order to acclimate them to human handling for the experiment. In addition, rats were trained to orally consume a liquid diet from a stainless steel bottle nipple with a ball bearing for the meal tolerance test.

The control carbohydrate challenge was a glucose solution at 1.0 g/kg body weight. Glucose was made into a 50 % (wt./vol.) solution with water prior to challenge. Similarly, the experimental carbohydrate challenge was a 50 % glucose solution made with supplemental fructose (0.16 g/kg body weight).

The two carbohydrate challenges were evaluated in a two-way crossover design over an 8 day period. At the time of testing, rats weighed 459±8.1 g (mean SEM) and were 17 weeks old. After an 18 hour overnight fast, rats underwent a meal tolerance test. On two different occasions, rats were randomly fed one of two carbohydrate solutions per os via bottle nipple. Formula volume was approximately 1 ml and was adjusted by animal weight such that each rat was delivered an equivalent glucose challenge on a body weight basis. Blood samples were collected at baseline and 30, 60, 90, 120, and 170 minutes postprandial for glucose analysis (Precision G; Medisense, Bedford, Mass.). Rats had free access to water throughout the experiment.

Blood samples were obtained via tail vein and collected into heparin containing capillary tubes (20 $\mu$l volume; Medisense). Approximately 5 $\mu$l of blood was immediately transferred directly onto a Precision G blood glucose test strip and analyzed for blood glucose concentration. Whole blood was used, however, the Precision G Instrument corrects the glucose measurement and provides the data as mg glucose/dl plasma.

Figure 2:
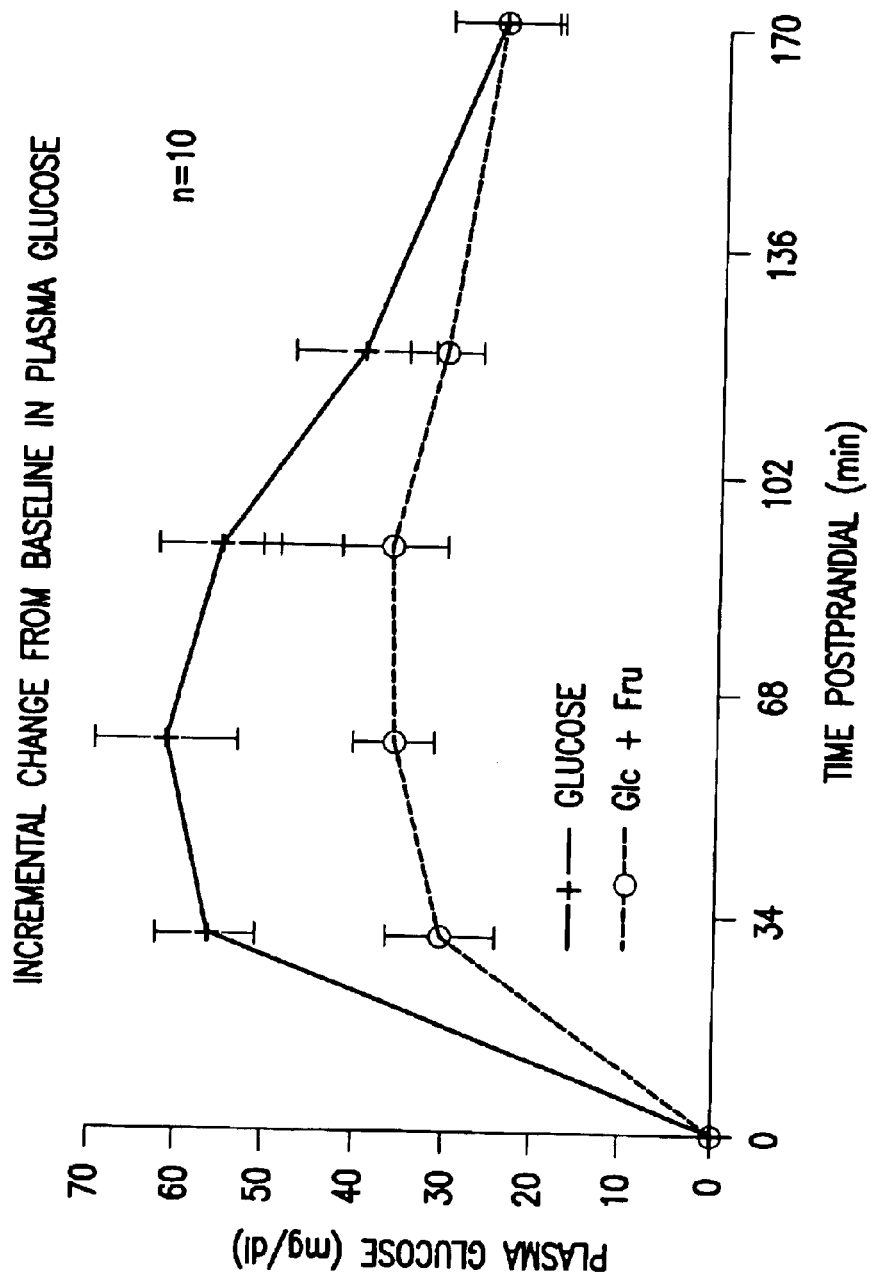
FIG. 2 is a graphical representation of the incremental change from baseline in blood glucose for rats fed glucose ± fructose as set forth in Example V.

The postprandial glycemic response of female Zucker fatty fa/fa rats fed glucose ± fructose can be found in FIG. 1 and the incremental change from baseline in blood glucose can be found in FIG. 2. Basal blood glucose values were not different (111±3 vs. 117±4 mg/dl; Glc vs. Glc+Fru, respectively). The incremental change from baseline in blood glucose was lower (P<0.05) for rats fed Gulc+Fru at 30, 60, and 90 minutes postprandial (FIG. 2). Area under the curve (AUC) was calculated (T.M.S. Wolever et. al., "The use of glycemic index in predicting the blood glucose response to mixed meals". AMERICAN JOURNAL OF CLINICAL NUTRITION, 1986, 43, 167–172). The supplemental fructose added to the glucose challenge reduced (P<0.05) the incremental AUC for blood glucose by 34% over the 3-hour experiment.

EXAMPLE VI

The objective of this experiment was to evaluate the postprandial glycemic response of male Zucker fatty fa/fa rats fed a partially hydrolyzed starch with supplemental fructose.

Ten male Zucker fatty fa/fa rats were obtained at five weeks of age from Harlan Sprague Dawley, Inc. (Indianapolis, Ind.). Rats were individually housed in microisolator cages on dry bedding and were given ad libitum access to water and rat chow (pelletted; 8640 Harlan Teklad 2215 Rodent Diet; Harlan Teklad, Madison, Wis.). The housing facility was maintained at 19° to 21° C., 30 to 70% relative humidity, and 12 hour light-dark cycle. Rats were handled 4 to 5 times per week for 8 weeks prior to this experiment in order to acclimate them to human handling for the experiment. In addition, rats were trained to orally consume a liquid diet from a stainless steel bottle nipple with a ball bearing for the meal tolerance test.

The control carbohydrate challenge was a partially hydrolyzed starch (Lodex 15; Gerestar USA, Inc., Hammond, Ind.) challenge at 1.0 g/kg body weight. The partially hydrolyzed starch was made into a 50 % (wt./vol.) solution with water prior to challenge. Similarly, the experimental carbohydrate challenge was a 50 % partially hydrolyzed starch solution made with supplemental fructose (0.16 g/kg body weight). Both treatments (10 ml total volume each) were heated in a microwave for 30 seconds at high to completely solublize the carbohydrate solutions 1 hour before testing.

The two carbohydrate challenges were evaluated in a two-way crossover design over a 9 day period. At the time of testing, rats weighed 494±6.7 g (mean±SEM) and were 14 weeks old. After a 16 hour overnight fast, rats underwent a meal tolerance test. On two different occasions, rats were randomly fed one of two carbohydrate solutions per os via bottle nipple. Formula volume was approximately 1 ml and was adjusted by animal weight such that each rat was delivered an equivalent digestible glucose polymer challenge on a body weight basis. Blood samples were collected at baseline and 30, 60, 90, 120, and 180 minutes postprandial for glucose analysis (Precision G; Medisense, Bedford, Mass.). Rats had free access to water throughout the experiment.

Blood samples were obtained via tail vein and approximately 5 $\mu$l of blood was immediately transferred directly onto a Precision G blood glucose test strip and analyzed for blood glucose concentration. Whole blood was used, however, the Precision G Instrument corrects the glucose measurement and provides the data as mg glucose/dl plasma.

Figure 3:
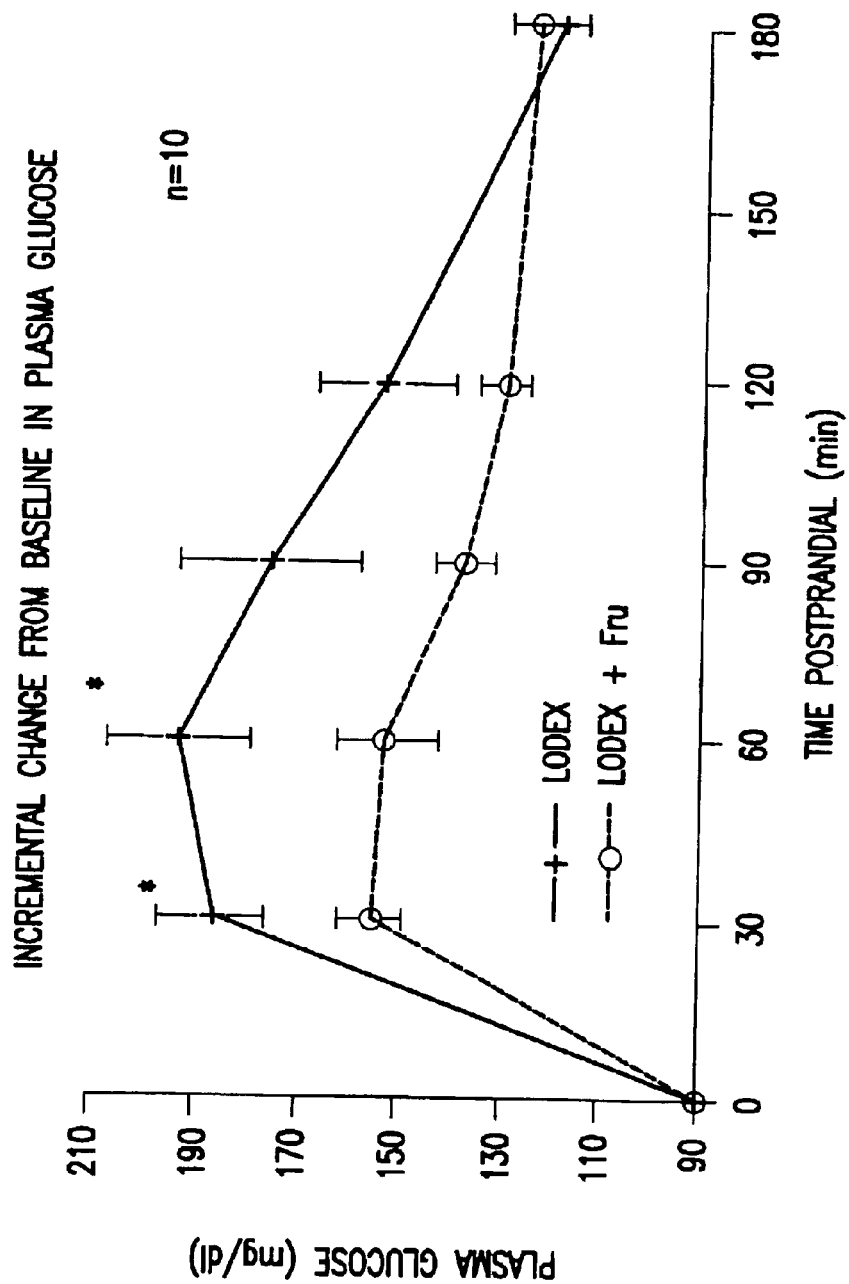
FIG. 3 is a graphical representation of the postprandial glycemic response of male Zucker fatty fa/fa rats fed partially hydrolyzed corn starch ± fructose as set forth in Example VI.
Figure 4:
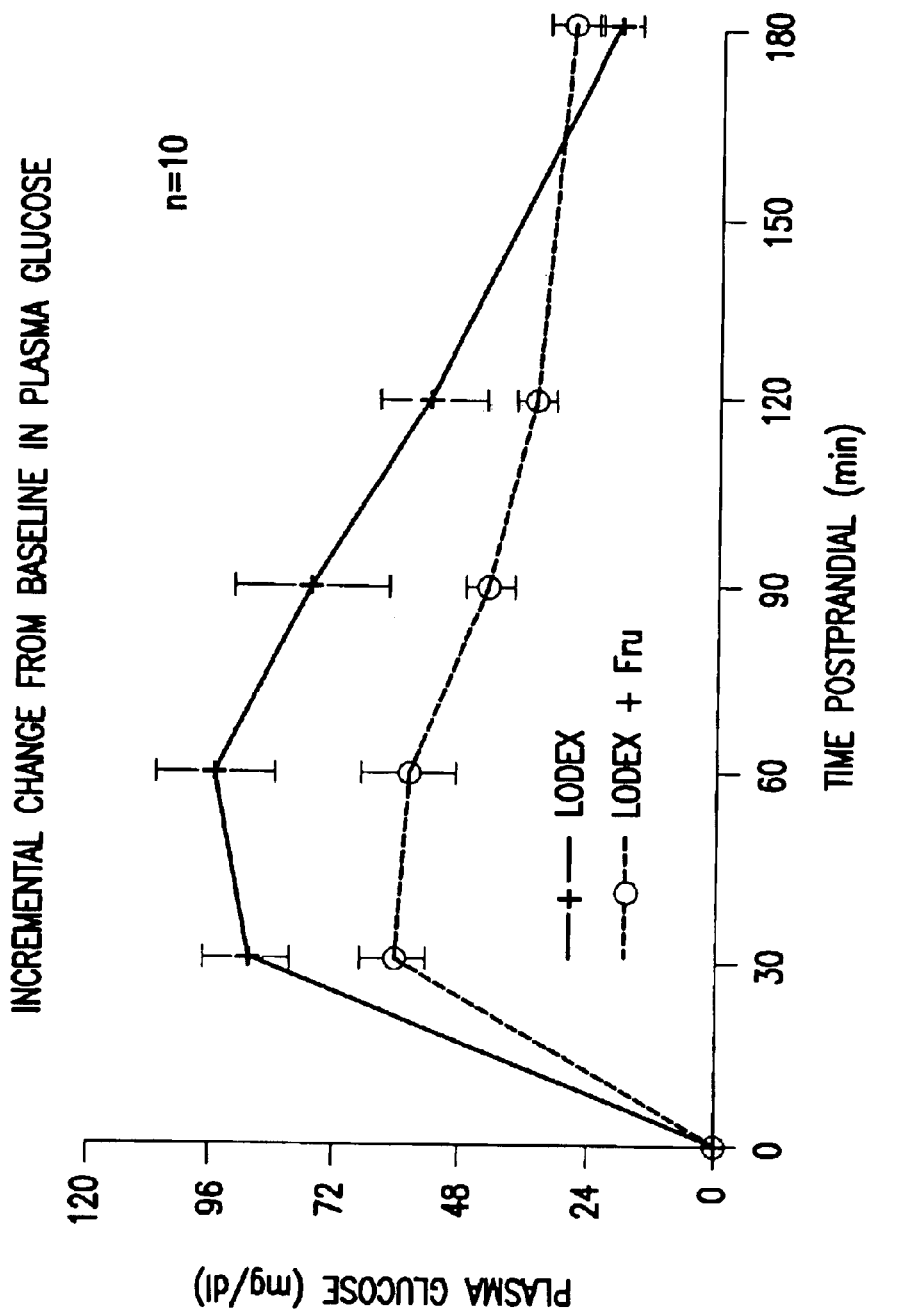
FIG. 4 is a graph of the incremental change from baseline in blood glucose for rats fed partially hydrolyzed corn starch ± fructose as set forth in Example VI.

The postprandial glycemic response of male Zucker fatty fa/fa rats fed partially hydrolyzed starch±fructose can be found in FIG. 3 and the incremental change from baseline in blood glucose can be found in FIG. 4. Basal blood glucose values were not different (97±4.6 vs. 93±2.4 mg/dl; partially hydrolyzed starch vs. partially hydrolyzed starch+Fru, respectively). The incremental change from baseline in blood glucose was lower (P<0.05) for rats fed partially hydrolyzed starch±Fru at 30, 60, and 90 minutes postprandial (FIG. 4). Area under the curve (AUC) was calculated (T.M.S. Wolever et. al., "The use of glycemic index in predicting the blood glucose response to mixed meals". AMERICAN JOURNAL OF CLINICAL NUTRITION, 1986, 43, 167–172). Supplemental fructose added to a partially hydrolyzed starch challenge reduced (P<0.05) the incremental AUC for blood glucose by 32% over the 3-hour experiment.

The embodiments of the present invention may, of course, be carried out in other ways than those set forth herein without departing from the spirit and scope of the invention. The present embodiments are, therefore, to be considered in all respects as illustrative and not restrictive and that all changes and equivalents also come within the description of the present invention.

We claim:

1. A nutritional product comprising:
   a) about 47% of the total calories of the product as a carbohydrate system, said carbohydrate system further comprises;
      i) about 23 wt/wt % of the carbohydrate system is a source of fructose,
      ii) about 64 wt/wt % of the carbohydrate system is digestible glucose polymers, iii) about 6.5 wt/wt % of the carbohydrate system is nonabsorbent carbohydrates,
iv) about 3 wt/wt % of the carbohydrate system is fiber selected from the group consisting of soluble fiber, insoluble fiber, fermentable fiber, non-fermentable fiber and mixtures thereof
v) about 3.5 wt/wt % of the carbohydrate system is indigestible oligosaccharides, b) a source of fat comprising about 33% of the total calories of the product and c) a source of protein comprising about 20% of the total calories of the product.

2. The nutritional product of claim 1 further including at least one additional nutrient selected from the group consisting of vitamin A, vitamin $B_1$, vitamin $B_2$, vitamin $B_6$, vitamin $B_{12}$, vitamin C, vitamin D, vitamin E, vitamin K, biotin, carnitine, taurine, folic acid, pantothenic acid, niacin, choline, calcium, phosphorus, magnesium, zinc, manganese, copper, sodium, potassium, chloride, iron, selenium, chromium and molybdenium.

3. A method for providing nutrition to an individual with diabetes comprising enterally administering the nutritional product according to claim 1.

4. A method for blunting the postprandial glycemic response comprising enterally administering the nutritional product according to claim 1.

* * * * *